United States Patent [19]

Obayashi et al.

[11] Patent Number: 4,972,019

[45] Date of Patent: Nov. 20, 1990

[54] WATER-ABSORBENT RESIN COMPOSITION

[75] Inventors: Shigeji Obayashi, Akashi; Morio Nakamura, Kakogawa; Takushi Yamamoto, Himeji; Hitoshi Tanaka, Himeji; Yuji Sakamoto, Himeji, all of Japan

[73] Assignee: Seitetsu Kagaku Co., Ltd., Japan

[21] Appl. No.: 368,795

[22] Filed: Jun. 20, 1989

Related U.S. Application Data

[62] Division of Ser. No. 53,623, May 26, 1987, Pat. No. 4,863,989.

[30] Foreign Application Priority Data

Jun. 4, 1986 [JP] Japan ................. 61-130567
Apr. 3, 1987 [JP] Japan ................. 62-083190

[51] Int. Cl.$^5$ ............................. C08K 5/46
[52] U.S. Cl. ........................... 524/83; 524/93; 524/167; 524/190; 524/288; 524/291; 524/418; 524/419; 524/421; 524/429
[58] Field of Search ............. 524/418, 419, 421, 429, 524/83, 93, 167, 190, 288, 291

[56] References Cited

U.S. PATENT DOCUMENTS

| | | | |
|---|---|---|---|
| 2,872,433 | 2/1959 | Glickman | 524/418 |
| 2,960,486 | 11/1960 | Pye | 524/421 |
| 3,079,357 | 2/1963 | Fischer | 524/421 |
| 3,108,990 | 10/1963 | Baxter | 524/418 |
| 3,261,798 | 7/1966 | Farley | 524/418 |
| 3,546,153 | 12/1970 | Mellan et al. | 524/421 |
| 3,801,675 | 4/1974 | Russell | 524/421 |
| 3,862,963 | 1/1975 | Hoshi et al. | 524/418 |
| 3,901,236 | 8/1975 | Assarsson et al. | 604/368 |
| 4,016,134 | 4/1977 | Machi | 524/419 |
| 4,080,351 | 3/1978 | Zalzal | 524/421 |
| 4,089,831 | 5/1978 | Chambers | 524/421 |
| 4,093,776 | 6/1978 | Aoki et al. | 428/402 |
| 4,286,082 | 8/1981 | Tsubakimoto et al. | 526/240 |
| 4,340,706 | 7/1982 | Obayashi et al. | 526/207 |
| 4,401,795 | 8/1983 | Herman et al. | 525/327.8 |
| 4,409,353 | 10/1983 | Umekawa et al. | 524/421 |
| 4,500,670 | 2/1985 | McKinley et al. | 524/445 |
| 4,507,438 | 3/1985 | Obayashi et al. | 525/119 |
| 4,525,527 | 6/1985 | Takeda et al. | 524/831 |
| 4,541,871 | 9/1985 | Obayashi et al. | 106/197.2 |
| 4,552,938 | 11/1985 | Mikita et al. | 526/240 |
| 4,581,405 | 4/1986 | Martischius et al. | 524/418 |
| 4,590,227 | 5/1986 | Nakamura et al. | 523/130 |
| 4,625,001 | 11/1986 | Tsubakimoto et al. | 526/88 |
| 4,654,039 | 3/1987 | Brandt et al. | 526/207 X |
| 4,655,202 | 4/1987 | Potter et al. | 524/418 |
| 4,666,983 | 5/1987 | Tsubakimoto et al. | 525/119 |
| 4,683,274 | 7/1987 | Nakamura etal. | 526/216 |

Primary Examiner—Joseph L. Schofer
Assistant Examiner—J. M. Reddick
Attorney, Agent, or Firm—Saidman, Sterne, Kessler & Goldstein

[57] ABSTRACT

A water-absorbent resin composition having superior gel stability which comprises a water-absorbent resin, at least one oxygen-containing reducing inorganic salt and, optionally, at least one organic antioxidant.

3 Claims, No Drawings

WATER-ABSORBENT RESIN COMPOSITION

This application is a division of application Ser. No. 053,623, filed May 26, 1987, now U.S. Pat. No. 4,863,989.

FIELD OF THE INVENTION

The present invention relates to a water-absorbent resin composition. More particularly, it relates to a water-absorbent resin composition having an improved stability to body fluids such as urine, catamenial blood, secretions and the like, and further relates to a water-absorbent resin composition having an improved stability to an aqueous solution containing an electrolyte in addition to an improved stability to body fluids.

BACKGROUND OF THE INVENTION

Recently, various water-absorbent resins have been developed (for example, see U.S. Pat. Nos. 4,340,706, 4,093,776, 4,459,396, 3,980,663 and 4,552,938) and have been extensively used in various water-absorbent articles such as diaper, menstrual articles and the like. Thereby, properties of water-absorbent articles are improved. For example, liquid retention characteristics are improved and liquid leak is diminished. Further, a comfortable feeling in wearing water-absorbent article which has absorbed body fluids is achieved. Accordingly, such a water-absorbent article tends to be kept on for a longer period of time.

On the other hand, it has been found that a gel resulted from absorption of fluids such as urine, catamenial blood, secretions and the like by a water-absorbent article is crumbled to be out of shape because, in general, a water-absorbent resin of the gel is decomposed by the body fluids with time. Accordingly, as a period of time for keeping a water-absorbent article on becomes longer, liquid retention characteristics of the article are lowered, which results in increase in liquid leak, impairment of feeling in wearing the article and the like. In view of this, it is required to develop a water-absorbent resin which has an improved gel stability to the body fluids.

As a means for improving a gel stability, for example, increase in crosslinking density of a water-absorbent resin may be employed. However, as crosslinking density becomes higher, a water-absorption capacity becomes lower and therefore it is necessary to increase an amount of the resin to be used. This is less economical and causes such a disadvantage that properties of a water-absorbent article are adversely affected.

OBJECTS OF THE INVENTION

Under these circumstances, the present inventors have studied intensively to obtain a water-absorbent resin having an improved gel stability to the body fluids. As the result, it has been found that a gel stability of a water-absorbent resin to the body fluids can be sufficiently improved without the above disadvantages by incorporation with an oxygen-containing reducing inorganic salt. Further, it has been found that, in addition to a gel stability to the body fluids, a gel stability of a water-absorbent resin to an aqueous solution containing an electrolyte can be also sufficiently improved with maintaining its high water-absorption capacity by incorporation with an organic antioxidant together with the oxygen-containing reducing inorganic salt.

That is, one object of the present invention is to provide a water-absorbent resin composition having an improved gel stability to the body fluids which is suitable for water-absorbent articles.

Another object of the present invention is to provide a water-absorbent resin composition having an improved gel stability to an aqueous solution containing an electrolyte as well as to the body fluids which is suitable for water-absorbent articles.

These objects as well as other objects and advantages of the present invention will become apparent to those skilled in the art from the following description.

SUMMARY OF THE INVENTION

In one aspect of the present invention, there is provided a water-absorbent resin composition which comprises a water-absorbent resin and at least one oxygen-containing reducing inorganic salt. This water-absorbent resin composition of the present invention has an improved gel stability to body fluids such as urine, catamenial blood, secretions and the like.

In another aspect of the present invention, there provides a water-absorbent resin composition which comprises a water-absorbent resin, at least one oxygen-containing reducing inorganic salt and at least one organic anitoxidant. This water-absorbent composition of the present invention has an improved stability to an aqueous solution containing an electrolyte in addition to an improved stability to the body fluids.

In the present invention, although an account of the mechanism of the oxygen-containing reducing inorganic salt and the organic antioxidant in the water-absorbent resin composition is unclear, properties of water-absorbent articles can be remarkably improved simply by incorporation of a small amount of these materials to the water-absorbent resin without any sanitary problem.

By using the composition of the present invention, there can be obtained various water-absorbent articles having improved properties such as improved liquid retention characteristics with good prevention of liquid leak and impairment of a feeling in wearing the article. Further, the composition of the present invention can be broadly used in the field where an aqueous solution containing an electrolyte is involved.

DETAILED DESCRIPTION OF THE INVENTION

The water-absorbent resin used in the composition of the present invention is not limited to a specific one and any conventional water-absorbent resin can be used. Examples of the water-absorbent resin include crosslinked polyacrylic acid salts, crosslinked copolymers of vinyl alcohol-acrylic acid salt, crosslinked saponification products of starch-acrylonitrile graft copolymer, crosslinked starch-acrylic acid salt copolymer, crosslinked products of polyvinyl alcohol grafted with maleic anhydride, crosslinked carboxymethyl cellulose alkali metal salt and the like.

In one aspect of the present invention, the water-absorbent resin is incorporated with the oxygen-containing reducing inorganic salt to improve its gel stability to body fluids such as urine, catamenial blood, secretions, etc.

As the oxygen-containing reducing inorganic salt in the present invention, particularly, there can be used at least one member selected from the group consisting of sulfites, bisulfites, pyrosulfites, dithionites, trithionates, tetrathionates, thiosulfates and nitrites. Specific examples of these oxygen-containing reducing inorganic salts include sulfites such as sodium sulfite, potassium sulfite, calcium sulfite, zinc sulfite, ammonium sulfite, etc.; bisulfites such as sodium bisulfite, potassium bisulfite, calcium bisulfite, ammonium bisulfite, etc.: pyrosulfites such as sodium pyrosulfite, potassium pyrosulfite, ammonium pyrosulfite, etc.; dithionites such as sodium dithionite, potassium dithionite, ammonium dithionite, calcium dithionite, zinc dithionite, etc.; trithionates such as potassium trithionate, sodium trithionate, etc.; tetrathionates such as potassium tetrathionate, sodium tetrathionate, etc.; thiosulfates such as sodium thiosulfate, potassium thiosulfate, ammonium thiosulfate, etc.: and nitrites such as sodium nitrite, potassium nitrite, calcium nitrite, zinc nitrite, etc. They can be used alone or in combination thereof. Among them, from the sanitary and gel stability points of view, sodium sulfite, sodium bisulfite, sodium pyrosulfite, sodium dithionite and sodium nitrite are preferred.

In the present invention, the oxygen-containing reducing inorganic salt is used in an amount of 0.001 to 10 parts by weight, preferably, 0.01 to 5 parts by weight per 100 parts by weight of the water-absorbent resin. When the amount of the reducing inorganic salt is less than 0.001 part by weight per 100 parts by weight of the water-absorbent resin, improvement of gel stability of the water-absorbent resin to the body fluids is scarcely expected. On the other hand, when the amount is more than 10 parts by weight, a water-absorption capacity of a resulting composition is lowered, while gel stability of the water-absorbent resin to the body fluids is improved.

In another aspect of the present invention, the water-absorbent resin is incorporated with both the oxygen-containing reducing agent and the organic antioxidant to improve its gel stability to both the body fluids and an aqueous solution containing an electrolyte such as physiological saline solution, artificial urine and the like.

In this aspect, the above-described oxygen-containing reducing agent can be used in an amount of the same range as described above in view of gel stability and a water-absorption capacity.

As the organic antioxidant, particularly, there can be used at least one member selected from the group consisting of ascorbic acid and its derivatives, gallic acid and its derivatives, benzothiazoles, dithionates, thiurams, benzimidazoles, formaldehyde sulfoxylates and phenothiazines. Specific examples of these organic antioxidant include ascorbic acid and its derivatives such as L-ascorbic acid, sodium L-ascorbate, isoascorbic acid, sodium isoascorbate, etc.: gallic acid and its derivatives such as gallic acid, methyl gallate, ethyl gallate, n-propyl gallate, isoamyl gallate, octyl gallate, lauryl gallate, etc.; benzothiazoles such as mercaptobenzothiazole, sodium mercaptobenzothiazole, zinc mercaptobenzothiazole, etc.; dithionates such as zinc methyldithiocarbamate, zinc diethyldithiocarbamate, zinc di-n-butyldithiocarbamate, zinc ethylphenyldithiocarbamate, etc.; thiurams such as tetramethylthiuram disulfide, tetraethylthiuram sulfide, tetrabutylthiuram disulfide, tetramethylthiuram monosulfide, etc.; benzimidazoles such as 2-mercaptobenzimidazole, etc.; formaldehyde sulfoxylates such as sodium formaldehyde sulfoxylate, etc.; and phenothiazines such as phenothiazine, 2-methoxyphenothiazine, etc. They can be used alone or in combination thereof. Among them, from the sanitary and gel stability points of view, L-ascorbic acid, sodium L-ascorbate, isoascorbic acid, sodium isoascorbate and n-propyl gallate are preferred.

In the present invention, the organic antioxidant is used in an amount of 0.0001 to 10 parts by weight, preferably, 0.001 to 5 parts by weight per 100 parts by weight of the water-absorbent resin. When the amount of the antioxidant is less than 0.0001 part by weight per 100 parts by weight of the water-absorbent resin, improvement of gel stability of the water-absorbent resin to an aqueous solution containing an electrolyte such as physiological saline solution or artificial urine is insufficient. On the other hand, when the amount is more than 10 parts by weight, gel stability of the water-absorbent resin becomes inferior. Further, when the water-absorbent resin is incorporated with only the antioxidant without incorporation of the oxygen-containing reducing inorganic salt, gel stability of the water-absorbent resin is rather lowered and therefore, in the present invention, the antioxidant should be used together with the inorganic salt.

The water-absorbent resin composition of the present invention can be prepared by blending the water-absorbent resin with the oxygen-containing reducing inorganic salt and, if necessary, the organic antioxidant. The blending method is not limited to specific one and any known method can be employed. For example, the inorganic salt and the antioxidant can be added to a polymerization reaction mixture of the water-absorbent resin. Further, they can be blended with the dried water-absorbent resin by so-called dry blending.

The water-absorbent resin composition of the present invention can be used for the production of various water-absorbent articles according to a conventional method.

The following Preparations, Comparative Examples and Examples further illustrate the present invention in detail but are not to be construed to limit the scope thereof.

PREPARATIONS

Preparation 1

Cyclohexane (213 g) was placed in a 500 ml four necked round bottom flask equipped with a stirrer, a reflux condenser, a dropping funnel and a nitrogen gas inlet. To the flask was charged sorbitan monolaurate having HLB of 8.6 (manufactured and sold by Nippon Oil and Fats Co., Ltd., Japan under the trade name of Nonion LP-20R)(1.9 g). After dissolution of the surfactant with stirring at room temperature, dissolved oxygen was purged with nitrogen gas.

Separately, a 80% (w/w) aqueous solution of acrylic acid (48.8 g) was placed in a 200 ml conical flask and a 25.9% (w/w) aqueous solution of sodium hydroxide (66.7 g) was added dropwise with cooling to neutralize 80 mole % of the acrylic acid. To the mixture was added potassium persulfate (0.13 g).

The resulting partially neutralized acrylic acid solution was added to the above four necked round bottom flask and the mixture was thoroughly purged with nitrogen gas. The mixture was heated and subjected to polymerization reaction for 3 hours while maintaining the bath temperature at 55° to 60° C.

Water and cyclohexane were distilled off and the residue was dried to obtain a fine granular water-absorbent resin (48.5 g).

Preparation 2 n-Heptane (280 ml) was placed in a 500 ml four necked round bottom flask equipped with a stirrer, a reflux condenser, a dropping funnel and a nitrogen gas inlet. To the flask was charged hexaglyceryl monobehenirate having HLB of 13.1 (manufactured and sold by Nippon Oil and Fats, Co., Ltd., Japan under the trade name of Nonion GV-106)(0.75 g). After dispersion of the surfactant, dissolved oxygen was purged with nitrogen gas. Temperature was raised to 50° C. to dissolve the surfactant and then the mixture was cooled to 30° C.

Separately, a 80% (w/w) aqueous solution of acrylic acid (37.5 g) was placed in a 200 ml conical flask and a 25.4% (w/w) aqueous solution of sodium hydroxide (49.3 g) was added dropwise with ice-cooling to neutralize 75 mole % of the acrylic acid. To the mixture was added potassium persulfate (0.045 g).

The resulting partially neutralyzed acrylic acid solution was added to the above four necked round bottom flask and the mixture was thoroughly purged with nitrogen gas. The mixture was heated and subjected to polymerization reaction for 2 hours while maintaining the bath temperature at 55° to 60° C.

Water and n-heptane were distilled off and the residue was dried to obtain a water-absorbent resin (40.2 g).

Preparation 3

A water-absorbent resin (40.3 g) was obtained according to the same manner as described in Preparation 2 except that ethylene glycol diglycidyl ether (0.038 g) was added to the polymerization reaction mixture.

COMPARATIVE EXAMPLES AND EXAMPLES

In the following Comparative Examples and Examples, absorbency, evaluation of gel stability to a saline solution (0.9% (w/w) aqueous solution of sodium chloride), preparation of an absorbent article and evaluation of gel stability to human urine were carried out as follows.

Absorbency

A water-absorbent resin (1 g) was dispersed in a 0.9% (w/w) aqueous solution of sodium chloride (200 ml) to thoroughly swell. After 4 hours or 15 hours, the swollen resin was filtered through a 100 mesh metallic wire gauze and the volume of the swollen resin obtained as a filter cake was measured and the value was taken as the absorbency.

Evaluation of gel stability to a saline solution

The swollen resin obtained in the above measurement of the absorbency was pressed with the fingers to organoleptically evaluate its gel stability according to the following four criteria.

A: Gel was not crumbled even by pressing strongly.
B: Gel was crumbled by pressing strongly.
C: Gel was observed but readily crumbled.
D: No gel form was retained.

Preparation of an absorbent article

A pulp having the basis weight of 150 g/m² was cut out to form a sheet (20 cm×10 cm) and a water-absorbent resin or a water-absorbent resin composition (3 g) was uniformly scattered thereon. Further, the same sheet as described above was laminated thereon and pressed by uniformly applying a pressure of 1 kg/cm² to obtain an absorbent article.

Evaluation of gel stability to human urine

Human urine (120 ml) was poured on the center part of the above-prepared absorbent article over 1 minute and the article was allowed to stand for 5 minutes. Then, the absorbent article which absorbed human urine was packaged in a polyethylene bag and the bag was placed in an incubator at 37° C. After 4 hours or 15 hours, the absorbent article was taken out of the bag and pressed with the fingers to organoleptically evaluate its gel stability according to the following four criteria.

A: Gel was not crumbled even by pressing strongly.
B: Gel was crumbled by pressing strongly.
C: Gel was observed but readily crumbled.
D: No gel form was retained.

COMPARATIVE EXAMPLES 1 to 5

By using the water-absorbent resins obtained in the above Preparations 1 to 3 and commercially available water-absorbent resins, Arasorb 720 (crosslinked polyacrylic acid salt manufactured and sold by Arakawa Chemical Co., Ltd., Japan) and Sanwet IM-1000 (crosslinked starch-acrylic acid salt graft copolymer manufactured and sold by Sanyo Chemical Industries Co., Ltd., Japan , the above measurement of absorbency, evaluation of gel stability to a saline solution, and evaluation of gel stability to human urine were carried out. The results are shown in Table 1.

COMPARATIVE EXAMPLE 6

A water-absorbent resin composition was prepared by thoroughly blending the water-absorbent resin power (40.0 g) obtained in the above Preparation 2 with L-ascorbic acid powder (0.4 g). By using the water-absorbent resin composition, the above measurement of absorbency, evaluation of gel stability to a saline solution, and evaluation of gel stability to human urine were carried out. However, no desired result could not be obtained.

TABLE 1

| Comp. Ex. No. | Water-absorbent resin | Absorbency (g/g) Aqueous 0.9% NaCl | | Evaluation of gel stability | | | |
|---|---|---|---|---|---|---|---|
| | | | | Aqueous 0.9% NaCl | | Human urine | |
| | | 4 hrs. | 15 hrs. | 4 hrs. | 15 hrs. | 4 hrs. | 15 hrs. |
| 1 | Prep. 1 | 85 | 85 | B | B | D | D |
| 2 | Prep. 2 | 70 | 70 | A | A | C | D |
| 3 | Prep. 3 | 50 | 50 | A | A | B | C |
| 4 | Arasorb 720 | 62 | 62 | B | B | C | D |
| 5 | Sanwet IM-1000 | 75 | 75 | B | B | D | D |

EXAMPLES 1 to 24

Various water-absorbent resin compositions were prepared by thoroughly blending the water-absorbent resins used in the above Comparative Examples with oxygen-containing reducing inorganic salts in various ratios. By using the water-absorbent resin compositions thus obtained, the above measurement of absorbency, evaluation of gel stability to a saline solution, and evaluation of gel stability to human urine were carried out. The results are shown in Tables 2A and 2B.

EXAMPLE 25

A water-absorbent resin composition (40.5 g) was obtained by addition of sodium sulfite (0.4 g) to the polymerization mixture of the above Preparation 2. By using the water-absorbent resin composition thus obtained, the above evaluation of gel stability to human urine was carried out. As the result, both evaluations after 4 hours and 15 hours were A.

TABLE 2A

| | Water-absorbent resin composition | | |
|---|---|---|---|
| | Water- | Oxygen-containing reducing inorganic salt | |
| Ex. No. | absorbent resin | Salt | Amount* (parts) |
| 1 | Prep. 1 | sodium sulfite | 0.5 |
| 2 | Prep. 1 | sodium dithionite | 1.5 |
| 3 | Prep. 1 | potassium nitrite | 4.0 |
| 4 | Prep. 1 | potassium pyrosulfite | 1.5 |
| 5 | Prep. 1 | sodium bisulfite | 4.0 |
| 6 | Prep. 2 | potassium bisulfite | 0.5 |
| 7 | Prep. 2 | sodium nitrite | 4.5 |
| 8 | Prep. 2 | calcium nitrite | 5.0 |
| 9 | Prep. 2 | sodium pyrosulfite | 2.0 |
| 10 | Prep. 2 | potassium bisulfite | 0.1 |
| 11 | Prep. 3 | sodium bisulfite | 1.0 |
| 12 | Arasorb 720 | potassium sulfite | 0.5 |
| 13 | Arasorb 720 | sodium dithionite | 3.5 |
| 14 | Sanwet IM-1000 | sodium sulfite | 0.05 |
| 15 | Sanwet IM-1000 | sodium sulfite | 1.0 |
| 16 | Sanwet IM-1000 | sodium sulfite | 5.0 |
| 17 | Prep. 1 | potassium bisulfite | 5.0 |
| 18 | Prep. 1 | sodium dithionite | 1.5 |
| 19 | Prep. 2 | sodium sulfite | 4.0 |
| 20 | Prep. 2 | calcium nitrite | 0.5 |
| 21 | Prep. 3 | sodium pyrosulfite | 1.0 |
| 22 | Prep. 3 | sodium bisulfite | 0.1 |
| 23 | Arasorb 720 | sodium sulfite | 3.5 |
| 24 | Sanwet IM-1000 | sodium sulfite | 2.0 |

Note:
*parts by weight per 100 parts by weight of the water-absorbent resin

TABLE 2B

| | Absorbency** (g/g) | | Evaluation of gel stability | | | |
|---|---|---|---|---|---|---|
| | Aqueous 0.9% NaCl | | Aqueous 0.9% NaCl | | Human urine | |
| Ex. No. | 4 hrs. | 15 hrs. | 4 hrs. | 15 hrs. | 4 hrs. | 15 hrs. |
| 1 | — | — | — | — | A | B |
| 2 | — | — | — | — | A | A |
| 3 | — | — | — | — | A | A |
| 4 | — | — | — | — | A | A |
| 5 | — | — | — | — | A | A |
| 6 | — | — | — | — | A | A |
| 7 | — | — | — | — | A | A |
| 8 | — | — | — | — | A | A |
| 9 | — | — | — | — | A | A |
| 10 | — | — | — | — | A | B |
| 11 | — | — | — | — | A | A |
| 12 | — | — | — | — | A | B |
| 13 | — | — | — | — | A | A |
| 14 | — | — | — | — | B | C |
| 15 | — | — | — | — | B | B |
| 16 | — | — | — | — | A | A |
| 17 | 96 | 32 | C | D | A | A |
| 18 | 120 | 76 | C | D | A | A |
| 19 | 78 | 99 | B | D | A | A |
| 20 | 106 | 53 | C | D | A | B |
| 21 | 103 | 47 | C | D | A | A |
| 22 | 55 | 118 | A | C | A | B |
| 23 | 71 | 95 | A | C | A | A |
| 24 | 87 | 120 | B | C | A | A |

Note:
**variance in absorbency is larger, gel is more unstable.

EXAMPLES 26 to 38

Various water-absorbent resin compositions were prepared by thoroughly blending the water-absorbent resins used in the above Comparative Examples with oxygen-containing reducing inorganic salts and organic antioxidants in various ratios. By using the water-absorbent resin compositions thus obtained, the above measurement of absorbency, evaluation of gel stability to a saline solution, and evaluation of gel stability to human urine were carried out. The results are shown in Tables 3A and 3B.

TABLE 3A

| | Water-absorbent resin composition | | | | |
|---|---|---|---|---|---|
| | Water absorbent | Oxygen-containing reducing inorganic salt | | Organic antioxidant | |
| Ex. No. | resin | Salt | Amount* (parts) | Compound | Amount* (parts) |
| 26 | Prep. 1 | potassium bisulfite | 5.0 | L-ascorbic acid | 0.002 |
| 27 | Prep. 1 | sodium sulfite | 1.0 | L-ascorbic acid | 0.02 |
| 28 | Prep. 1 | ammonium pyrosulfite | 2.8 | zinc ethylphenyldithiocarbamate | 1.3 |
| 29 | Prep. 2 | sodium sulfite | 4.0 | phenothiazine | 0.8 |
| 30 | Prep. 2 | sodium sulfite | 1.0 | n-propyl gallate | 5.0 |
| 31 | Prep. 2 | calcium nitrite | 0.5 | n-propyl gallate | 1.0 |
| 32 | Prep. 2 | calcium nitrite | 4.7 | n-propyl gallate | 1.0 |
| 33 | Prep. 3 | sodium pyrosulfite | 1.0 | mercaptobenzothiazole | 0.3 |
| 34 | Prep. 3 | sodium bisulfite | 0.1 | 2-mercaptobenzimidazole | 0.1 |
| 35 | Arasorb 720 | potassium sulfite | 3.5 | tetramethylthiuram disulfide | 3.0 |
| 36 | Arasorb 720 | sodium dithionite | 1.1 | sodium formaldehyde sulfoxylate | 4.8 |
| 37 | Sanwet IM-1000 | sodium sulfite | 2.0 | sodium isoascorbate | 0.005 |
| 38 | Sanwet IM-1000 | sodium sulfite | 2.0 | sodium isoascorbate | 0.1 |

Note:
*parts by weight per 100 parts by weight of the water-absorbent resin

TABLE 3B

| | Absorbency** (g/g) | | Evaluation of gel stability | | | |
|---|---|---|---|---|---|---|
| | Aqueous 0.9% NaCl | | Aqueous 0.9% NaCl | | Human urine | |
| Ex. No. | 4 hrs. | 15 hrs. | 4 hrs. | 15 hrs. | 4 hrs. | 15 hrs. |
| 26 | 83 | 83 | B | B | A | A |
| 27 | 84 | 84 | B | B | A | A |
| 28 | 85 | 85 | B | B | A | A |
| 29 | 68 | 68 | A | A | A | A |
| 30 | 69 | 70 | A | A | A | A |
| 31 | 70 | 70 | A | A | A | A |
| 32 | 67 | 66 | A | A | A | A |
| 33 | 50 | 50 | A | A | A | A |
| 34 | 50 | 50 | A | A | A | A |
| 35 | 58 | 57 | A | A | A | A |
| 36 | 59 | 59 | A | A | A | A |
| 37 | 74 | 74 | B | B | A | A |
| 38 | 74 | 74 | B | B | A | A |

Note:
**variance in absorbency is larger, gel is more unstable.

As seen from Tables 1, 2A and 2B, the water-absorbent resin composition of the present invention comprising the water-absorbent resin and the oxygen-containing reducing inorganic salt has superior gel stability to the body fluid in comparison with the water absorbent resin alone. Further, as seen from Table 1, 3A and 3B, the water-absorbent resin composition of the present invention comprising the water-absorbent resin, the oxygen-containing reducing inorganic salt and the organic antioxidant has superior gel stability to both the body fluid and an aqueous soution containing an electrolyte in comparison with the water absorbent resin alone.

What is claimed is:

1. A water-absorbent resin composition which comprises
   (a) crosslinked polyacrylic acid salts, crosslinked copolymers of vinylalcohol-acrylic acid salt, crosslinked saponification products of starch-acrylonitrile graft copolymer, crosslinked starch-acrylic acid salt copolymer, crosslinked products of polyvinylalcohol grafted with maleic anhydride, or crosslinked carboxymethyl cellulose alkali metal salts;
   (b) at least one oxygen-containing reducing inorganic salt selected from the group consisting of sulfites, bisulfites, pyrosulfites, dithionitres, trithionates, tetrathionates, thiosulfates, and nitrites; and
   (c) at least one organic antioxidant selected from the group consisting of ascorbic acid and its derivatives, gallic acid and its derivatives, benzothiazoles, dithionates, thiurams, benzimidazoles, formaldehyde sulfoxylates and phenothiazines.

2. A water-absorbent resin composition according to claim 1, wherein the composition contains the oxygen-containing reducing inorganic salt in an amount of 0.001 to 10 parts by weight per 100 parts by weight of the water-absorbent resin.

3. A water-absorbent resin composition according to claim 1, wherein the composition contains the organic antioxidant in an amount of 0.0001 to 10 parts by weight per 100 parts by weight of the water-absorbent resin.

* * * * *